United States Patent [19]

Hirschfeld et al.

[11] Patent Number: 4,803,049

[45] Date of Patent: Feb. 7, 1989

[54] PH-SENSITIVE OPTRODE

[75] Inventors: Tomas B. Hirschfeld, Livermore; Francis T. Wang, Danville, both of Calif.

[73] Assignee: The Regents of the University of California, Berkeley, Calif.

[21] Appl. No.: 681,487

[22] Filed: Dec. 12, 1984

[51] Int. Cl.[4] .................. G01N 21/80; G01N 33/49
[52] U.S. Cl. ..................................... 422/58; 128/633; 128/634; 128/637; 128/639; 250/227; 356/39; 422/68; 436/163; 436/172
[58] Field of Search ............. 422/55, 57, 58, 68; 436/163, 172, 800; 435/181; 128/634, 637, 639, 633; 356/39; 250/227

[56] References Cited

U.S. PATENT DOCUMENTS

| Re. 31,879 | 5/1985 | Lübbers et al. ............... 422/58 X |
| 3,904,373 | 9/1975 | Harper ....................... 436/169 X |
| 4,003,707 | 1/1977 | Lübbers et al. ............... 422/83 X |
| 4,033,330 | 7/1977 | Willis et al. ................. 128/633 |
| 4,041,932 | 8/1977 | Fostick ....................... 128/633 |
| 4,075,493 | 2/1978 | Wickersheim . |
| 4,200,110 | 4/1980 | Peterson et al. . |
| 4,215,275 | 7/1980 | Wickersheim . |
| 4,245,507 | 1/1981 | Samulski . |
| 4,269,516 | 5/1981 | Lübbers et al. ............... 356/39 X |
| 4,344,438 | 8/1982 | Schultz . |
| 4,447,546 | 5/1984 | Hirschfeld . |
| 4,454,229 | 6/1984 | Zander ....................... 436/163 X |
| 4,557,900 | 12/1985 | Heitzmann ................... 422/87 X |
| 4,577,109 | 3/1986 | Hirschfeld ................... 250/461.1 |

FOREIGN PATENT DOCUMENTS 2303803  7/1982  European Pat. Off. .

OTHER PUBLICATIONS

Wickersheim and Alves, "Recent Advances in Optical Temperature Measurement," *Ind. Research & Development* Dec. (1979).

Primary Examiner—Benoit Castel
Assistant Examiner—Jill Johnston
Attorney, Agent, or Firm—Michael B. K. Lee; Stephen C. Maceviz

[57] ABSTRACT

An apparatus is provided for remotely monitoring pH. A support material is provided on which organic dye molecules are covalently attached at a surface density falling within a predetermined range. The pH dependent fluorescence response of the bound organic dye molecules depends critically on surface density of the organic dye molecules bound to the support material and the nature of the covalent linkage between the organic dye molecules and the support material. The invention is operated by contacting the support material on which the organic dye is attached with the fluid whose pH is to be determined. When in contact, the organic dye on the support material is illuminated so that it is caused to fluoresce. The intensity of organic dye fluorescence is then related to pH.

44 Claims, 3 Drawing Sheets

PH-SENSITIVE OPTRODE

BACKGROUND OF THE INVENTION

The United States Government has rights in this invention pursuant to Contract No. W-7405-ENG-48 between the U.S. Department of Energy and the University of California, for the operation of Lawrence Livermore National Laboratory.

The invention relates to optical means for remotely monitoring pH and, particularly, for invasive, or direct, monitoring of blood pH.

In medicine, invasive, or direct, monitoring of blood acid-base parameters and other selected ions is desirable, and in many cases necessary, in the management of critically ill patients or those undergoing complex surgical procedures. In particular, blood pH is regulated within very narrow bounds in normal individuals, varying no more than several hundredths of a pH unit from an average of 7.40. The pH is directly dependent on bicarbonate and dissolved $CO_2$ concentrations in the blood. As a consequence, several anesthetic agents and diseases affect blood pH, either directly or indirectly. In particular, diabetic acidosis, which arises from depletion of serum bicarbonate, and pulmonary disorders and anesthetic agents, which affect respiration, can cause rapidly increased blood $pCO_2$, which in turn can produce striking alterations in blood pH. Either of these events are life threatening. Thus, there is an important medical need for directly monitoring blood pH.

Currently, the most widespread methods for direct blood pH measurement, or direct blood electrolyte monitoring, involve the use of ion-selective electrodes. While such electrodes can provide rapid and accurate measurements, there are several disadvantages to their use. The familiar glass pH electrode does not readily lend itself to the construction of invasive devices. Although miniature glass electrodes have been mounted on flexible catheters, small glass electrodes are inherently fragile and therefore present serious risks to the patient. Indeed, most investigators of in vivo blood pH have not employed invasive electrodes, but rather have adopted the somewhat more cumbersome technique in which an arterial-venous shunt is constructed to allow blood flow past a rigidly mounted, mechanically protected glass electrode.

Electrical interference is a major problem with high-resistance microelectrodes such as glass electrodes. Low-resistance miniature electrodes are available, and can give satisfactory measurements in the presence of other electrical equipment, but these require that the amplifying and processing electronics be physically close to the electrodes. Thus, the capability for remote measurements is lost. The most common electrical interference occurs in the 50-60 Hz and radio frequency ranges. While such interference can be reduced by special filtering electronics, both forms of interference can cause DC shifts which are easily overlooked.

Finally, the use of currently available electrodes can present direct hazards to patient safety. Electronically based transducers can pose an electrical hazard, especially when other such transducers are used at the same time, and polyvinyl chloride-based electrodes widely used with inophores, such as valinomycin, can be dissolved by many gaseous anesthetics.

The electrical interference problem of electrodes is not limited to their uses in medicine. In any environment where high sensitivity is critical, electrical noise generated by extraneous fields will be a problem. Other problems inherent to the use of electrodes include the susceptibility of wire leads and couplings to deterioration under corrosive conditions, or conditions of alternating temperatures.

Many of the above-mentioned difficulties with current information-gathering technology can be overcome by using remote, in situ optical probes coupled to a detector by optical waveguides, or fiber optics, e.g., Hirschfeld, "Remote Fiber Fluorimetric Analysis," *Energy and Technology Review*, pgs. 17–21 (July 1980); Borman, "Optrodes," *Anal. Chem.*, Vol. 53, pgs. 1616A–1618A (December 1981); and Peterson and Vurek, "Fiber Optic Sensors for Biomedical Applications," *Science*, Vol. 224, pgs. 123–129 (Apr. 13, 1984). Fiber optics are durable, corrosion-resistant, heat-resistant, impervious to electrical or magnetic interference, and are available in very small diameters, which makes them amenable for use with miniature probes.

Peterson, et al., in U.S. Pat. No. 4,200,110, issued Apr. 29, 1980, disclose a pH sensing device which employs an optical transducer connected to a detector by two fiber optics. The optical transducer is a membranous-walled chamber which contains particles on which colorimetric pH sensitive dyes are attached or impregnated. The dye is illuminated by white light transmitted by one fiber optic, and the light scattered by the dye-covered particles is collected by the other fiber optic. Use of more than one fiber optic reduces sensitivity because precise alignment of the illuminating and light-collecting fibers must be maintained, and because illumination of dye molecules is less efficient when separate fibers are used for illumination and collection than if a single fiber is used for both collection and illumination. Moreover, the presence of the membrane between the pH-sensitive dye and the fluid being monitored substantially reduces the response time of the device to rapid changes in pH.

Numerous workers have used fluorescein or other dyes bound to solid supports as quantitative pH indicators. Haaijman and Van Dalen, "Quantification in Immunofluorescence Microscopy: A New Standard for Fluorescein and Rhodamine Emission Measurement," *Journal of Immunological Methods*, Vol. 5, pgs, 359–374 (1974), quantified the fluorescent response of fluorescein bound to Sephadex supports to changes in pH. Hirschfeld, in Borman, "Optrodes," cited above, reported binding fluorescein to porous glass supports for the purpose of measuring pH, futher results being reported in Hirschfeld et al., "Feasibility of Using Fiber Optics for Monitoring Groundwater Contaminants," *Optical Engineering*, Vol. 22, pgs, 527–531 (October 1983). Saari and Seitz, in *Analytical Chemistry*, Vol. 54, pgs. 821–823 (April 1982), disclose a pH sensor based on fluorescence generated by a fluoresceinamine immobilized on a controlled pore glass support. Immobilization was achieved by reacting controlled pore glass derivatized with isothiocyanate groups with a saturated solution of fluoresceinamine. Saari and Seitz report that their procedure for immobilizing fluoresceinamine reduces the intensity of the fluorescent signal by approximately three orders of magnitude from that of a comparable amount of unbound fluoresceinamine. They also report an extremely unfavorable signal-to-noise ratio of approximately 1:2 at pH 3.

The foregoing illustrates the limitations of the current pH-sensing technology, especially in the area of medical applications. An alternative to available pH sensing methods which overcame some of these limitations would be highly advantageous for remote pH-sensing applications, particularly in situ monitoring of blood pH.

SUMMARY OF THE INVENTION

It is therefore an object of the invention to provide a pH-sensing apparatus which generates an optical signal related to the magnitude of the pH sensed.

Another object of the invention to provide a pH-sensing apparatus which generates an optical signal related to the magnitude of the pH sensed and which transmits said optical signal to a detector by a fiber optic.

Another object of the invention is to provide a low cost, low maintenance pH sensor capable of remotely monitoring pH and compatible with a multi-position monitoring system utilizing optical sensors.

Another object of the invention is to provide an optically based pH sensor capable of monitoring the pH of physiological fluids, particularly blood.

These and other objects are attained in accordance with the present invention wherein a support material is provided on which organic dye molecules are covalently attached at a surface density falling within a predetermined range. The invention is an application of the discovery that the pH dependent fluorescent response of bound organic dye molecules depends critically on (1) the surface density of organic dye molecules bound to the support material and (2) the nature of the covalent linkage between the organic dye molecules and the support material. The invention is operated by contacting the support material on which the organic dye is attached with the fluid whose pH is to be determined. When in contact, the organic dye on the support material is illuminated so that it is caused to fluoresce. The intensity of organic dye fluorescence is then related to pH.

Preferably the invention comprises a fiber optic for transmitting an illumination beam to the organic dye molecules and for collecting the fluorescence thereof, and preferably the support material is in the form of a particle, hereinafter referred to as a carrier particle. An illumination beam is transmitted from a first end of the fiber optic to a second end of the fiber optic, the illumination beam comprising light from at least one associated light source. A carrier particle with covalently bonded organic dye molecules is attached to the second end of the fiber optic so that light from the illumination beam emanating from the second end causes the covalently bound organic dye molecules to fluoresce. The organic dye molecules are attached to the carrier particle at a surface density within the predetermined range. A portion of the fluorescence from the bound organic dye molecules is collected by the second end of the fiber optic and transmitted to the first end of the fiber optic, the transmitted portion of the fluorescence comprising a fluorescent signal. At the first end of the fiber optic the fluorescent signal is separated from the illumination beam and analyzed.

The present invention is addressed to problems associated with remote pH monitoring in hostile or inaccessible regions. It advantageously overcomes many of these problems by combining rugged, high quality fiber optics with simple in situ transducers for generating fluorescent signals related to ambient pH. For pH measurements in physiological fluids, the problem of poor signal-to-noise ratio is overcome by adjusting the surface density of organic dye molecules bound to a carrier particle so that it falls within a predetermined range characterized by a strong fluorescent response in the range of physiological pHs.

In addition, all particular embodiments of the invention are amenable for use with a multi-position sensing system which comprises many sensors, all of which feed signals to a single station for analysis. Such a configuration can reduce costs by obviating the need for separate analyzers for each sensor, and can increase reproducibility between sensors by having all signals analyzed by the same instrument.

BRIEF DESCRIPTION OF THE DRAWINGS

Further objects of the invention, together with additional features conbtributing thereto and advantages accruing therefrom will be apparent from the following descriptions of preferred embodiments of the invention which are shown in the accompanying drawings, which are incorporated in and form a part of the specification. In the drawings.

DETAILED DESCRIPTION OF THE INVENTION

Reference will now be made in detail to the present preferred embodiments of the invention, an example of which is illustrated in the accompanying drawings.

In accordance with the present invention an apparatus is provided for measuring pH by means of an in situ fluorescent probe which generates a fluorescent signal whose intensity varies with ambient pH. The fluorescent probe comprises a support material onto which a plurality of organic dye molecules are covalently attached so that there is a sufficient number of non-dimerized organic dye molecules on the support material to generate a fluorescent signal. A minimum number of organic molecules that do not form dimers is at least $10^3$ attached molecules. A sufficient number of these organic molecules that do not form dimers and generate a fluorescent signal since they are illuminated by the illumination beam is at least $10^3$ attached molecules. The invention is operated by first placing the fluorescent probe in contact with the fluid whose pH is to be determined, i.e., an associated fluid. Next, the fluorescent probe is caused to fluoresce by illuminating it with light from a suitable light source. A portion of the resulting fluorescence is then collected, and its intensity is related to pH.

Preferably the support material is in the form of a particle, hereinafter referred to as a carrier particle, attached to an end of a fiber optic. In accordance with this embodiment an illumination beam from an associated light source is transmitted from a first end of the fiber optic to a second end of the fiber optic, the carrier particle being attached to the second end of the fiber optic so that light from the illumination beam emanating from the second end illuminates the carrier particle causing the attached organic dye molecules to fluoresce. A portion of the generated fluorescence is collected by the second end of the same fiber optic and transmitted to the first end of the fiber optic, the transmitted fluorescence forming a fluorescent signal. At the first end of the fiber optic the fluorescent signal is separated from the illumination beam and analyzed.

Many different support materials and many different techniques for covalently attaching organic dye molecules, such as fluorescein, are available for use in accordance with the present invention. Such materials and techniques are well known in the arts of affinity chromatography and enzyme immobilization technology, e.g., Jakoby and Wilchek, editors "Affinity Techniques," *Methods in Enzymology*, Vol. 34 (Academic Press, NY, 1974), Mobach, editor, "Immobilized Enzymes," *Methods in Enzymology*, Vol. 44 (Academic Press, NY, 1976), and Maugh II, *Science*, Vol. 223, pgs. 474-476 (Feb. 3, 1984). Among support materials, inorganic support materials, such as controlled-pore glass, are preferred. Inorganic support material suitable for use in accordance with the present invention are described by Messing and Weetall, U.S. Pat. No. 3,519,538 issued July 7, 1970, entitled, "Chemically Coupled Enzymes," Weetall, U.S. Pat. No. 3,652,761 issued Mar. 28, 1972, entitled "Immunochemical Composites and Antigen or Antibody Purification Therewith," and Weetall, "Covalent Coupling Methods for Inorganic Support Materials," in *Methods of Enzymology*, Vol. 44, pgs. 134-148 (Academic Press, NY, 1976). Accordingly, these references are incorporated by reference for their descriptions of inorganic support materials and means for covalently coupling organic molecules thereto.

The preferred means of covalently bonding organic dye molecules to an inorganic support material is by way of a silane coupling agent. Silane coupling agents are silicon compounds which possess two different kinds of reactivity: organofunctional and siliconfunctional. That is, silane coupling agents have a silicon portion with an affinity for inorganic materials such as glass or aluminum silicate, and they have an organic portion which may be tailored to combine with a variety of other organics, such as fluorescein, or some suitably derivatized version thereof, such as fluorescein isothiocyanate. The most preferred support material is controlled-pore glass. Controlled pore glass is commercially available in a variety of forms manufactured according to the techniques of Hood et al., U.S. Pat. No. 2,106,764, Chapman et al., U.S. Pat. No. 3,485,687, and Haller, U.S. Pat. No. 3,549,524. Moreover, it is commercially available in a variety of pore sizes and with a variety of different silane coupling agents already attached (Pierce Chemical Company, *Handbook and General Catalog*, Rockford, IL, 1983). Alternatively, silane coupling agents suitable for use with the present invention can be prepared and attached to control pore glass in accordance with the teaching of Weetall and Filbert, "Porous Glass for Affinity Chromatography Applications," in *Methods of Enzymology*, Vol. 34, pgs. 59-72 (Academic Press, NY, 1974). Accordingly, this article is incorporated by reference.

Aminopropyl and aminoaryl silane coupling agents having formulas —O$_3$Si(CH$_2$)$_3$NH$_2$ and respectively, are preferred.

A crucial feature of the present invention is the requirement that the organic dye molecules be attached to the support material such that a sufficient number of the molecules remained non-dimerized for a fluorescent signal to be generated. It has been discovered that when certain organic dyes are attached to a support material at high surface densities adjacent dye molecules interact, and in so doing reduce the fluorescence response of the interacting molecules. It is believed that this interaction involves the formation of dimers, akin to the dimerization process described by Chambers et al., in "Effect of Dimer Formation on the Electronic Absorption and Emission Spectra of Ionic Dyes, Rhodamines and Other Common Dyes," *J. Physical Chemistry*, Vol. 78, pgs 380-387 (1974).

In accordance with the invention any organic dye whose fluorescence is substantially reduced by dimerization is amenable for use in the invention. In particular, this class of dyes includes sulforhodamine, rhodamine, eosin B, eosin Y, acriflavine, proflavine acridine orange, and fluorescein. Fluorescein is the preferred organic dye for measuring pH in the physiological range.

In accordance with the invention the fluorescent probe comprising the support material and bound organic dye molecules can be characterized either by the number of non-dimerized covalently attached fluorescein molecules present, or by the average density of bound organic dye molecules (whether dimerized or not). In the latter case the approximate length of the coupling agent must be known and the bound organic dye must be uniformly and substantially randomly distributed on the surface of the support material. The number of non-dimerized organic dye molecules covalently attached to a support material is referred to as the first plurality of organic dye molecules. The number of organic dye molecules covalently attached to a support material uniformly and substantially randomly distributed at a density within a preferred range is referred to as the second plurality of organic dye molecules.

At least two factors determine the preferred range of densities for particular support materials and coupling agents: the surface density of the coupling agent on the support material, and the length and flexibility of the coupling with an attached organic dye molecule. The surface density of organic dye molecules covalently attached to a support material can be expressed in any convenient units, e.g., molecules per square micrometer, or the like. If attached dye molecules are distributed uniformly and substantially randomly on the surface of the support material and if the approximate length of the coupling agent is known, then the probability that there will be an attached organic dye molecule within interaction distance of any given attached dye molecule can be readily computed, e.g., Pielou, *An Introduction to Mathematical Ecology* (Wiley-Interscience, NY, 1969) pgs. 111-123, which pages are incorporated by reference. From this probability the number of non-interacting attached organic dye molecules can be computed, and an expected fluorometric response estimated. Thus, for a given support material and coupling agent an upper limit on organic dye molecule surface density can be computed. The lower limit of organic dye molecule surface density is determined by detector sensitivity and noise level. The upper and lower limits define an operable, or preferred, range of surface densities. Within the operable range there is a most preferred surface density where there is a maximum of non-interacting organic dye molecules.

The nature of the surface of the support material is important in determining the lower limit of preferred surface densities: the greater amount of available surface area per illuminated region of support material the lower the limit of operable densities. For example, controlled-pore glass possesses a highly convoluted surface, and its surface area per volume is exceedingly high. Thus, the lower limit of the preferred density range for controlled-pore glass is substantially lower than that of other support materials, such as crosslinked polymers, and the like. In all cases, however, the density within the illumination-collection region must be high enough so that there is a sufficient number of organic dye molecules to generate a fluorescent signal. By way of example, current detection apparatus can readily detect a fluorescent signal from as few as $10^3$ fluorescein molecules, Haaijman and Van Dalen, "Quantification in Immunofluorescence Microscopy: A New Standard for Fluorescein and Rhodamine Emission Measurement," *Journal of Immunological Methods*, Vol. 5, pgs. 359–374 (1974).

To insure that the surface density of organic dye molecules lie within the operable range, either the surface density of coupling agents can be controlled, or the reaction between the coupling agents and the organic dye (or suitable derivatives thereof) can be controlled. The latter alternative is particularly applicable when commercially available derivatized controlled-pore glass is used, as the surface density of the coupling agents is quite high.

If the surface density of coupling agents is relatively sparse so that interaction between organic dye molecules is precluded (or minimal), then the coupling agents can be completely reacted with the organic dye, saturating the coupling agents with organic dye molecules. If the surface density of the coupling agents is relatively high, then procedures must be chosen which prevent saturation of the coupling agents with organic dye molecules. Such prevention can be accomplished using standard chemical techniques such as disabling some of the coupling agents (for example by including a reactant which competes with the organic dye for coupling agent reaction cites, but which does not substantially affect the fluorescence output of the organic dye), or adjusting reaction times, reactant concentrations, and the like.

Non-specific binding or adsorption is a common problem in procedures for covalently bonding molecules to support materials. That is, in many cases the molecule to be covalently bonded also has an affinity for ionic or hydrogen bonding with the support material. A washing step is typically required to remove non-specifically bonded molecules from the support material. PaDraig et al., in "Interfering and Complicated Adsorption Effects in Bioaffinity Chromatography," *Methods in Enzymology*, Vol. 34 (Academic Press, NY, 1974) pgs. 108–126, and Messing, in "Adsorption and Inorganic Bridge Formations," *Methods in Enzymology*, Vol. 44 (Academic Press, NY, 1976) pgs. 148–169, discuss the adsorption phenomena and techniques for removing adsorbed molecules. Accordingly, these articles are incorporated by reference. Where the predominant cause of adsorption is ionic bonding, the standard technique for removal is washing in a concentrated salt solution, e.g., NaCl or KCl.

Once organic dye molecules are attached to a suitable support material at an operable surface density techniques for causing the attached organic dye molecules to fluoresce and for collecting and analyzing the resultant fluorescence are well known in the art of fluorometry, e.g., Hercules, editor, Chapter 2, in *Fluorescence and Phosphorescence Analysis* (Interscience Publications, NY, 1966), White and Argauer, Chapter 2, in *Fluorescence Analysis* (Marcel Dekker, Inc., NY, 1970), and Parker, Chapter 3, in *Photoluminescence of Solutions* (Elsevier Publishing Company, NY, 1968). Accordingly, the respective chapters of these books are incorporated by reference.

Figure 1:
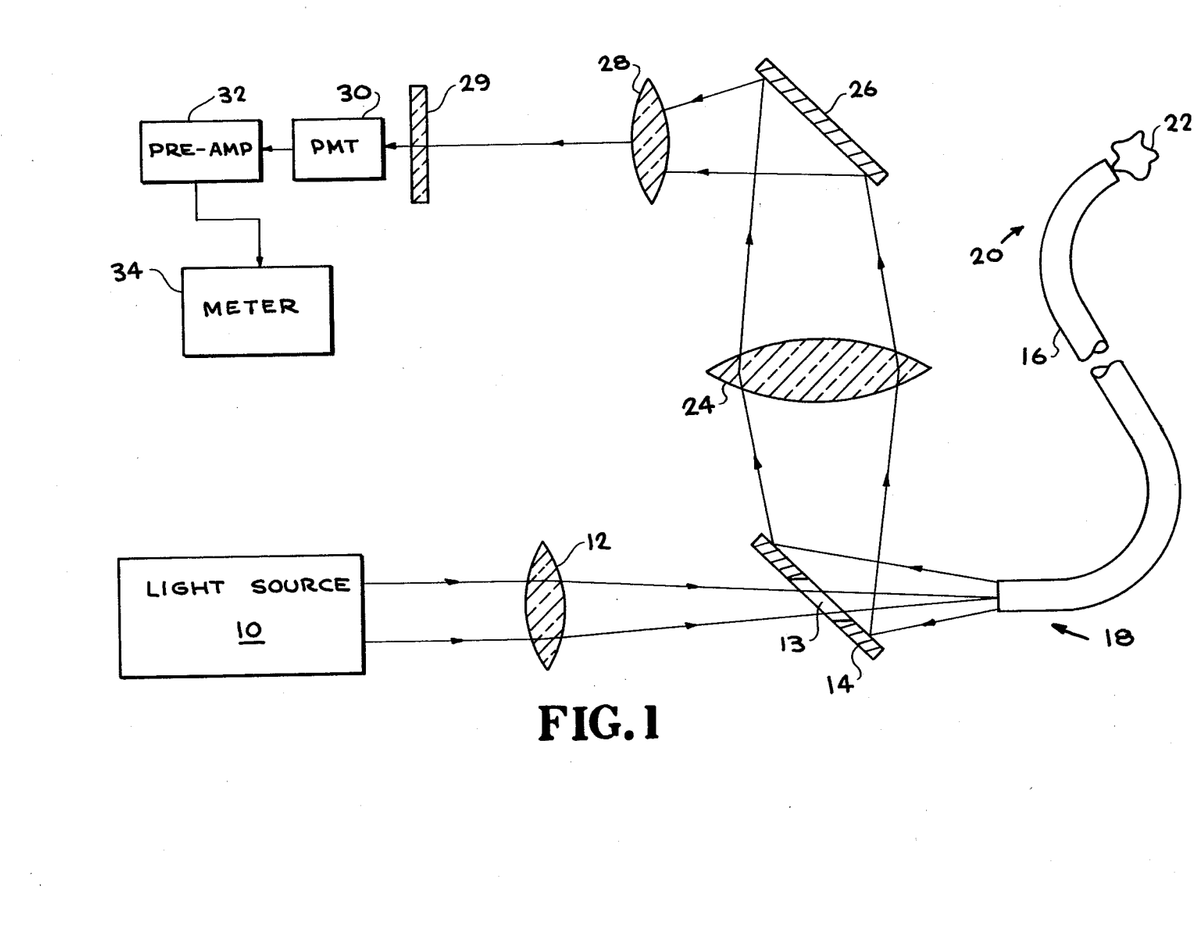
FIG. 1 diagrammatically illustrates an optical configuration suitable for use with the present invention.

As mentioned above the preferred embodiment of the invention comprises support material in the form of a carrier particle which is attached to the end of a fiber optic. FIG. 1 diagrammatically illustrates an optical configuration suitable for use with a preferred embodiment. An illumination beam generated by light source 10 is focussed by lens 12 and directed to first end 18 of fiber optic 16. Preferably light source 10 is a laser operating at a wavelength suitable for inducing the organic dye to fluoresce, e.g., an argon-ion laser operating at 488 nm for fluorescein. Most preferably, light source 10 is a mode-locked laser generating pulses in the nanosecond range, or less. Pulsed output is preferable over continuous output because very high peak power can be achieved with relatively low average power, thereby maximizing fluorescent output while minimizing the chance of heat damage to system components, e.g., fiber optic 16, carrier particle 22, and the means for attaching the carrier particle to the fiber optic. The focal length of lens 12 is relatively long so that the angle of incidence of the illumination beam as it enters fiber optic 16 is within the acceptance angle of the fiber optic. This ensures that all of the illumination beam will be transmitted by fiber optic 16. Fiber optic 16 preferably is a step index type communications fiber optic, such as a Valtec PC-10 (Valtec Corp., West Boylstrom, MA), or the like; although this is not a critical requirement of the invention, and other types of fiber optics can be used. Preferably the average diameter of carrier particle 22 is at least the magnitude of the diameter of the core of fiber optic 16. Most preferably the average diameter of carrier particle 22 is between about 1–3 times the diameter of the core of fiber optic 16.

The illumination beam exits fiber optic 16 at second end 20 so that the organic dye molecules on carrier particle 22 are caused to fluoresce. A portion of the fluorescence is collected by fiber optic 16 at second end 20 and transmitted to first end 18. Adjacent to first end 18 apertured mirror 14 separates the "outgoing" illumination beam from the "incoming" fluorescent signal. Lens 24 collects the fluorescent signal and focusses it on collimating lens 28 via a mirror 26. The fluorescent signal then passes through band-pass filter 29 and is collected by photomultiplier tube 30. Band-pass filter 29 is chosen to restrict the light incident on the photomultiplier tube 30 to that which has wavelengths corresponding to those of the fluorescent emission distribution of the organic dye. For example, if the organic dye is fluorescein and if light source 10 is an argon ion laser operating at 488 nm, band-pass filter 29 can be chosen to pass light at wavelengths greater than 500 nm and less than 550 nm/. Under these conditions scattered light from the illumination beam is prevented from reaching photomultiplier tube 30. Output from photomultiplier tube 30 is amplified by preamplifier 32. The output of preamplifier 32 can be read directly on meter 34, or the output can be manipulated further by a data processing means which provides a direct pH readout related to the intensity of the fluorescent signal.

Figure 2:
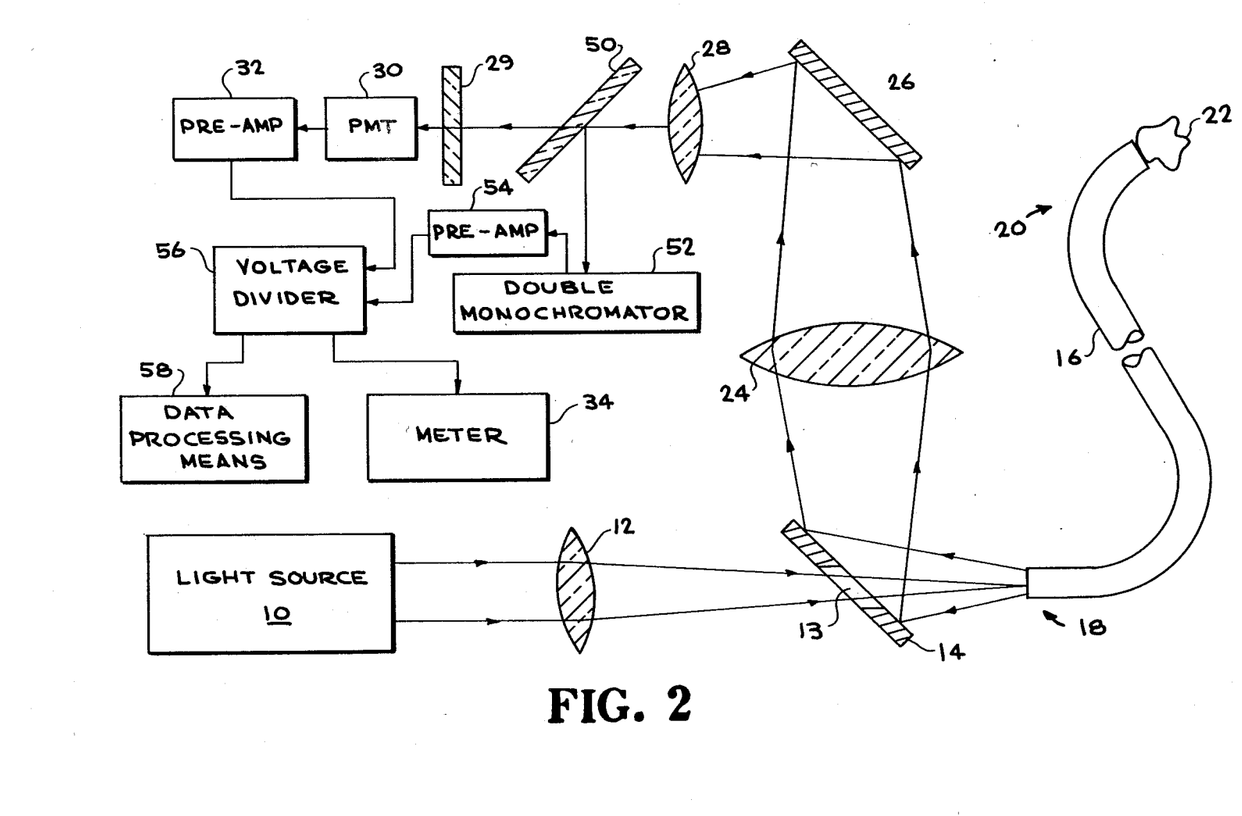
FIG. 2 diagrammatically illustrates an optical configuration which includes means for monitoring Raman backscatter from the fiber optic.

The accuracy of the pH determination can be improved by providing means for monitoring the Raman emission from the fiber optic caused by the illumination beam. In particular, the intensity of Raman emissions backscattered and transmitted to first end 18 can be monitored. The intensity of the backscattered Raman emissions depends directly on the intensity of the illumination beam and the length of the fiber optic. By monitoring the ratio of the intensity of the fluorescent signal to the intensity of the collected Raman backscatter, errors due to fluctuations in illumination beam intensity are automatically factored out. That is, in an embodiment employing Raman backscatter measurements, a fluorescent signal-Raman backscatter intensity ratio is related to pH. Techniques for measuring Raman backscatter are well known in the art of Raman spectroscopy, e.g., Chapter 2 entitled "Experimental Methods," in Tobin, *Laser Raman Spectroscopy* (Wiley-Interscience, NY, 1971) describes suitable apparatus. Accordingly, this chapter is incorporated by reference. FIG. 2 illustrates an optical configuration which includes means for monitoring Raman backscatter. Between collimating lens 28 and band-pass filter 29 beam splitter 50 diverts a portion of the light collected by collection lens 24. The diverted portion is then directed to double monochromator 52 (e.g., model 1430, Spex Corporation, Metuchen, NJ), or like instrument, for measuring the intensity of the Raman backscatter. Output from double monochromator 52 is preamplified by preamplifier 54 and received by analog voltage divider 56. Likewise the output of preamplifier 32 is received by analog voltage divider 56. The output of analog voltage divider 56 is directly related to the fluorescence intensity—Raman backscatter intensity ratio, and can be read off of meter 34 or can be converted to a pH readout by data processing means 58.

The following examples illustrate methods of constructing the preferred embodiment for different choices of support material.

EXAMPLE I

Figure 3:
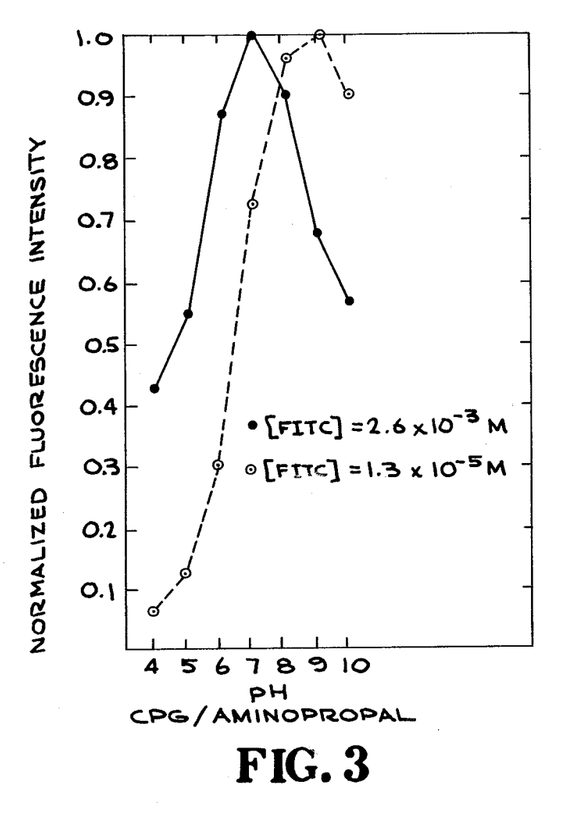
FIG. 3 is a curve describing the relationship between fluorescence intensity and pH for an embodiment of the invention employing fluorescein covalently linked to a controlled-pore glass carrier particle via aminopropyl silane coupling agents.

A controlled pore glass carrier particle was employed. Carrier particle diameter was within the range of 122 to 177 μm, average pore diameter was 500 angstroms, expected surface area was 70 m²/gram, and the carrier particle was derivatized with aminopropyl coupling agents at an approximate surface density of $13.8-15.5 \times 10^{13}$ coupling agents per square centimeter. The chemical structure of the aminopropyl coupling agent is described in Weetall and Filbert, "Porous Glass for Affinity Chromatography Applications," *Methods in Enzymology*, Vol. 34, pgs. 59–72. Carrier particles of this type are available from Pierce Chemical Company (Rockford, IL), product number 23909. The derivatized carrier particle was attached to the end of a 250 μm. core diameter Valtec 441 fiber optic, which end was cleaved with a diamond cutter to obtain a flat and clear surface. The carrier particle was glued to the end of the fiber optic by a UV-cured optical adhesive (NoA 61, Norland Products, Inc., New Brunswick, NJ). After the carrier particle was attached, it was dipped into a $1.3 \times 10^{-5}$M aqueous solution of fluorescein isothiocyanate (e.g., available from Aldrich Chemical Company, Milwaukee, WI) for about 20–30 minutes, followed by soaking in water for about 30–60 minutes. The pH response of the resulting sensor was tested by measuring pHs of several solutions buffered at predetermined pHs. The attached fluorescein was illuminated by an argon ion laser tuned to 488 nm at 2 microwatts. FIG. 3 illustrates relative fluorescence intensity versus pH for this embodiment.

EXAMPLE II

Figure 4:
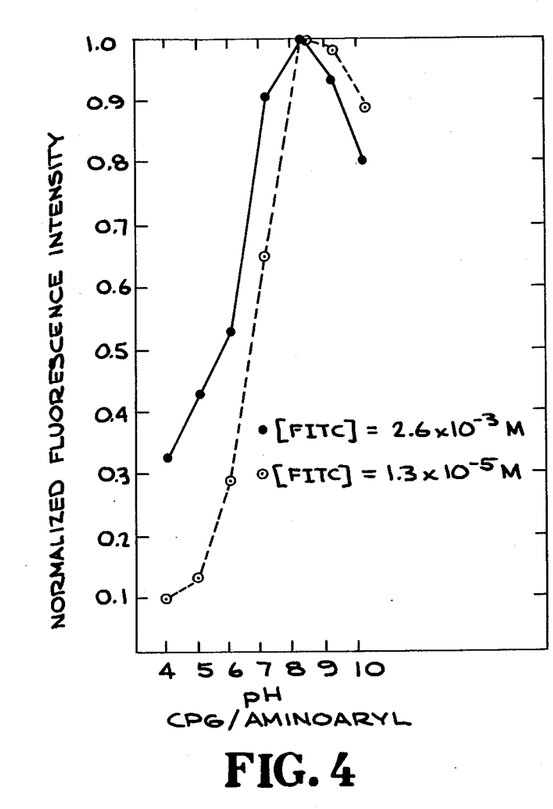
FIG. 4 is a curve describing the relationship between fluorescence intensity and pH for an embodiment of the invention employing fluorescein covalently linked to a controlled-pore glass carrier particle via aminoaryl silane coupling agents.

A controlled-pore glass carrier was employed, the carrier particle having a diameter within the range of about 122–177 μm, an average pore diameter of about 500 angstroms, average surface area per gram of about 70 square meters, and being derivatized with an aminoaryl coupling agent at an approximate surface density of about $21.5-34.4 \times 10^{12}$ coupling agents per square centimeter. The chemical structure of the aminoaryl coupling agent is described in Weetall and Filbert, "Porous Glass for Affinity Chromatography Applications," *Methods in Enzymology*, Vol. 34, pgs. 59–72. This type of carrier particle is commercially available from Pierce Chemical Company (Rockford, IL), product number 23415. The aminoaryl-derivatized carrier particle was attached to the end of the Valtec 441 250 μm core diameter fiber optic as in Example I. After attachment the carrier particle was dipped into a $1.3 \times 10^{-5}$M aqueous solution of fluorescein isothiocynate as in Example I, followed by soaking in water as in Example I. The pH response was measured in an identical manner as that of the embodiment described in Example I. FIG. 4 illustrates relative fluorescence intensity versus pH for this embodiment.

EXAMPLE III

Sephadex G-25 carrier particles (Pharmacia Fine Chemicals, Uppsula, Sweden) are aminated with aminoethylsulphuric acid. Carrier particles are suspended in 2M NaOH. After swelling (minimally 3 hours), the suspension is centrifuged for 1 minute at 3000 times the force of gravity in a graded centrifuge tube. The supernatant is removed by suction and a solution containing 0.1 g aminoethylsulfuric acid (Fluka AG, Buchs, Switzerland) per ml 2M NaOH is added at four times the volume of the packed carrier particles. The mixture is incubated at 85° C. for between 15 minutes and 24 hours. After incubation, the carrier particles are washed on a sintered glass funnel first with 200 ml 1M NaOH; then with a large volume of distilled water, and finally with 0.05M carbonate buffer, pH 9.5. The carrier particles are dried after washing with acetone. One milligram fluorescein isothiocyanate is dissolved in 100 ml of carbonate buffer; pH 9.5. 10 ml of freshly prepared fluorescein isothiocyanate solution is added to 1 ml sedimented carrier particles. The carrier particles are incubated in the solution at room temperature for between 1–60 minutes. Afterwards the carrier particles are washed three times with 15 ml 0.05M carbonate buffer, pH 9.5, three times with 15 ml PBS, pH 7.2. Dried carrier particles are attached to the end of a 250 μm core diameter Valtec 441 fiber optic as described in Example I.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. An apparatus for monitoring the pH of an associated fluid, the apparatus comprising:
   a light source for generating an illumination beam;
   a support material having a surface, the surface being capable of contacting the associated fluid;
   a first plurality of rhodamine or fluorescein dye molecules covalently attached to the surface of the support material, the attached rhodamine or fluorescein dye molecules of the first plurality being spaced on the surface of the support material so that dimers are not formed between the attached rhodamine or fluorescein dye molecules of the first plurality and adjacent attached rhodamine or fluorescein dye molecules, and the first plurality comprising a sufficient number of attached rhodamine or fluorescein dye molecules so that a fluorescent signal is generated whenever the attached rhodamine or fluorescein dye molecules of the first plurality are illuminated by the illumination beam; and
   detection means for detecting the fluorescent signal and for relating the intensity thereof to the pH of the associated fluid.

2. The apparatus as recited in claim 1 wherein said rhodamine or fluorescein dye molecules are fluorescein molecules.

3. The apparatus as recited in claim 2 wherein said first plurality includes at least $10^3$ covalently attached fluorescein molecules.

4. The apparatus as recited in claim 3 wherein said first plurality includes at least $10^4$ covalently attached fluorescein molecules.

5. The apparatus as recited in claim 4 wherein said first plurality includes at least $10^5$ covalently attached fluorescein molecules.

6. The apparatus as recited in claim 5 wherein said first plurality includes at least $10^6$ covalently attached fluorescein molecules.

7. The apparatus as recited in claim 2 wherein said sufficient number of attached fluorescein molecules of said first plurality is at least $10^3$.

8. The apparatus as recited in claim 7 wherein said sufficient number of attached fluorescein molecules of said first plurality is at least $10^4$.

9. The apparatus as recited in claim 8 wherein said sufficient number of attached fluorescein molecules of said first plurality is at least $10^5$.

10. The apparatus as recited in claim 9 wherein said sufficient number of attached fluorescein molesules of said first plurality is at least $10^6$.

11. The apparatus as recited in claim 1 wherein said support material is in the form of a carrier particle, and wherein said apparatus further comprises:
    a fiber optic through which said illumination beam from said light source is transmitted from a first end of the fiber optic to a second end of the fiber optic, the carrier particle being attached to the second end of the fiber optic so that light emanating from the second end of the fiber optic causes said attached rohdamine or fluorescein dye molecules of said first plurality to fluoresce, and so that a portion of the fluorescence generated by said attached rohdamine or fluorescein dye molecules of said first plurality is collected by the second end of the fiber optic and transmitted to the first end of the fiber optic, the transmitted portion of the generated fluorescence forming said fluorescent signal; and
    means associated with the first end of the fiber optic for separating the fluorescent signal from said illumination beam.

12. The apparatus as recited in claim 11 wherein said rhodamine or fluorescein dye molecules are fluorescein molecules.

13. The apparatus as recited in claim 12 wherein said sufficient number of attached fluorescein molecules of said first plurality is at least $10^3$.

14. The apparatus as recited in claim 13 wherein said sufficient number of attached fluorescein molecules of said first plurality is at least $10^4$.

15. The apparatus as recited in claim 14 wherein said sufficient number of attached fluorescein molecules of said first plurality is at least $10^5$.

16. The apparatus as recited in claim 15 wherein said sufficient number of attached fluorescein molecules of said first plurality is at least $10^6$.

17. The apparatus as recited in claim 11 wherein said rhodamine or fluorescein dye molecules are fluorescein dye molecules and wherein said detection means includes means for monitoring the intensity of Raman emission of said fiber optic caused by the transmission of said illumination beam through said fiber optic, and data processing means for forming a ratio of the intensity of the Raman emissions of said fiber optic to the intensity of said fluorescent signal and for relating the ratio of the pH of said associated fluid.

18. The apparatus as recited in claim 17 wherein said sufficient number of attached fluorescein molecules of said first plurality is at least $10^3$.

19. The apparatus as recited in claim 18 wherein said sufficient number of attached fluorescein molecules of said first plurality is at least $10^4$.

20. The apparatus as recited in claim 19 wherein said sufficient number of attached fluorescein molecules of said first plurality is at least $10^5$.

21. The apparatus as recited in claim 20 wherein said sufficient number of attached fluorescein molecules of said first plurality is at least $10^6$.

22. An apparatus for monitoring the pH of an associated fluid, the apparatus comprising:
    a light source for generating an illumination beam;
    a support material having a surface, the surface being capable of contacting the associated fluid;
    a second plurality of rhodamine or fluorescein dye molecules spaced uniformly and substantially randomly on the surface of the support material at an effective density for generating a fluorescent signal, each rhodamine or fluorescein dye molecule being covalently attached to the surface of the support material by a coupling agent, the coupling agent having a mean length, and a portion of the rhodamine or fluorescein dye molecules of the second plurality being caused to fluoresce by the illumination beam so that the fluorescent signal is generated; and detection means for detecting the fluorescent signal and for relating the intensity thereof to the pH of the associated fluid.

23. The apparatus as recited in claim 22 wherein said support material is the form of a carrier particle, the carrier particle having an average diameter, and wherein said apparatus further comprises:

a fiber optic through which said illumination beam from said light source is transmitted from a first end of the fiber optic to a second end of the fiber optic, the carrier particle being attached to the second end of the fiber optic so that light emanating from the second end of the fiber optic causes said attached rhodamine or fluorescein dye molecules of said second plurality to fluoresce, and so that a portion of the fluorescence generated by said attached rhodamine or fluorescein dye molecules of said second plurality is collected by the second end of the fiber optic and transmitted to the first end of the fiber optic, the transmitted portion of the generated fluorescent forming said fluorescence signal; and means associated with the first end of the fiber optic for separating the fluorescent signal from said illumination beam.

24. The apparatus as recited in claim 23 wherein said fiber optic has a core diameter and wherein said average diameter of said carrier particle is greater than or equal to the core diameter of said fiber optic.

25. The apparatus as recited in claim 24 wherein said average diameter of said carrier particle is between about 1-3 times said core diameter of said fiber optic.

26. The apparatus as recited in claim 25 wherein said means length of said coupling agent is about 5 angstroms.

27. The apparatus of claim 26 wherein said rhodamine or fluorescein dye molecules are fluorescein molecules.

28. The apparatus as recited in claim 27 wherein said effective density is between about $10^{-1}$–$10^7$ fluorescein molecules per square micrometer.

29. The apparatus of claim 28 wherein said effective density is between about $10^3$–$10^7$ fluorescein molecules per square micrometer.

30. The apparatus of claim 28 wherein said carrier particle is made of controlled-pore glass and said coupling agent is a silane coupling agent.

31. The apparatus of claim 30 wherein said carrier particle of controlled-pore glass has an average pore diameter of about 500 angstroms.

32. The apparatus of claim 25 wherein said means length of said coupling agent is between about 10-20 angstroms.

33. The apparatus of claim 32 wherein said rhodamine or fluorescein dye molecules are fluorescein molecules.

34. The apparatus of claim 33 wherein said effective density is between about $10^{-1}$–$10^6$ fluorescein molecules per square micrometer.

35. The apparatus of claim 34 wherein said carrier particle is made of controlled-pore glass and said coupling agent is a silane coupling agent.

36. The apparatus of claim 35 wherein said carrier particle of controlled-pore glass has an average pore diameter of about 500 angstroms.

37. The apparatus of claim 35 wherein said silane coupling agent is aminopropyl.

38. The apparatus of claim 35 wherein said silane coupling agent is aminoaryl.

39. The apparatus of claim 34 wherein said effective density is between about $10^2$–$10^6$ fluorescein molecules per square micrometer.

40. The apparatus of claim 39 wherein said predetermined range of densities is between about $10^4$–$10^5$ fluorescein molecules per square micrometer.

41. The apparatus of claim 40 wherein said carrier particle is made of controlled-pore glass and said coupling agent is a silane coupling agent.

42. The apparatus of claim 41 wherein said carrier particle of controlled-pore glass has an average pore diameter of about 500 angstroms.

43. The apparatus of claim 42 wherein said silane coupling agent is aminopropyl.

44. The apparatus of claim 42 wherein said silane coupling agent is aminoaryl.

* * * * *